United States Patent
Sovesky et al.

(10) Patent No.: US 9,827,601 B2
(45) Date of Patent: Nov. 28, 2017

(54) EFFICIENT DECONTAMINATION OF PERSONNEL AND OBJECTS

(71) Applicant: FLIR Detection, Inc., Pittsburgh, PA (US)

(72) Inventors: Robert J. Sovesky, Sharon, PA (US); Jason Robosky, Pittsburgh, PA (US); Jeremy P. Walker, Oakmont, PA (US); Markus Erbeldinger, Pittsburgh, PA (US)

(73) Assignee: FLIR Detection, Inc., Stillwater, OK (US)

( * ) Notice: Subject to any disclaimer, the term of this patent is extended or adjusted under 35 U.S.C. 154(b) by 85 days.

(21) Appl. No.: 14/733,084

(22) Filed: Jun. 8, 2015

(65) Prior Publication Data
US 2016/0354812 A1    Dec. 8, 2016

(51) Int. Cl.
| | | |
|---|---|---|
| *B08B 7/04* | (2006.01) | |
| *B08B 3/08* | (2006.01) | |
| *B08B 3/02* | (2006.01) | |
| *B08B 1/00* | (2006.01) | |
| *B08B 13/00* | (2006.01) | |

(52) U.S. Cl.
CPC .............. *B08B 7/04* (2013.01); *B08B 1/001* (2013.01); *B08B 3/02* (2013.01); *B08B 3/08* (2013.01); *B08B 13/00* (2013.01)

(58) Field of Classification Search
CPC ......... B08B 3/00; B08B 3/0408; B08B 1/001; B08B 3/02; B08B 3/048; B08B 3/08; B08B 7/00; B08B 7/04; B08B 13/00; E02D 31/00
USPC .............................. 134/18, 26; 588/260, 261
See application file for complete search history.

(56) References Cited

U.S. PATENT DOCUMENTS

| | | | |
|---|---|---|---|
| 4,934,396 A | 6/1990 | Vitta | |
| 6,630,105 B1 | 10/2003 | O'Neill et al. | |
| 7,163,589 B2 | 1/2007 | Kaiser | |
| 2003/0102007 A1* | 6/2003 | Kaiser ...................... | B08B 3/02 134/1 |
| 2004/0065350 A1* | 4/2004 | Achar ...................... | A61K 8/49 134/18 |
| 2010/0227345 A1* | 9/2010 | LeJuene ................... | C12Q 1/28 435/12 |

FOREIGN PATENT DOCUMENTS

WO    WO-2001-095341    12/2001

* cited by examiner

*Primary Examiner* — Saeed T Chaudhry
(74) *Attorney, Agent, or Firm* — Wells St. John P.S.

(57) ABSTRACT

A method for efficiently decontaminating surfaces is provided comprising applying an indicator to a surface wherein the indicator provides an observable or machine readable response when a contamination is present on the surface, wherein the response is located relative to a location of the contamination; and decontaminating the location of the contamination, and optionally rechecking the location of the initial contamination post decontamination to ensure that the surface is free of contamination.

9 Claims, 4 Drawing Sheets

EFFICIENT DECONTAMINATION OF PERSONNEL AND OBJECTS

GOVERNMENT INTEREST

Certain embodiments of this invention were made with Government support under Contract Nos. HDTRA1-10-C-0034 and HDTRA1-07-C-0075 awarded by the Defense Threat Reduction Agency (DTRA). The Government has certain rights in the invention.

FIELD OF THE INVENTION

A system and method for efficient decontamination is provided. It includes methods for locating contamination in order to focus decontamination processes where the contamination may be located. Another embodiment includes efficient surface decontamination methods.

BACKGROUND OF THE INVENTION

Exposure to Chemical Warf are Agents (CWAs), toxic industrial chemicals, and biological agents poses a threat to those around them. The armed forces can face potential exposure during combat operations. Mustard Gas was used during WWI. The Tokyo subway was attacked with Sarin gas in 1995. Recently, Sarin gas was confirmed to have been used on Syrian civilians by the state, resulting in hundreds of deaths in 2013. Further, most CWAs are odorless and colorless making them difficult to find; contact with trace quantities can cause permanent health damage, while exposure to larger concentrations of these chemicals can cause severe acute symptoms and even death. Thus, it is desirable for the military or for a first responder to have the ability to quickly determine the location of toxic chemical contamination so it can be marked to be avoided and/or rapidly and efficiently decontaminated.

CWAs are generally delivered as aerosols or in ordnance and can deposit on personnel, vehicles, shelters, soil and other surfaces. They could be delivered in a combat scenario or even in a domestic terrorism attack. This makes it of upmost importance that the contamination is located and removed from the surfaces. This is typically done through treating the entire surface with decontaminating solutions.

Current methods for decontamination may require large amounts of water and decontamination formulation. In operation, this may require those performing decontamination to have to move, deliver, and store copious amounts of water and solution where they have set up their decontamination line. Further, these solutions may be toxic themselves and/or strong oxidizers.

While performing decontamination procedures, operators ordinarily wear Hazmat suits. These suits are usually cumbersome, hot and difficult to maneuver. The operators try to minimize their time in these suits.

Additionally, many decontamination efforts may not sufficiently destroy a substantial amount of the agent present. The agent could be absorbed into the surface, stuck in cracks, or missed completely. Ensuring substantial contamination was removed may reduce health risks to personnel who may come into future contact with the contaminated surfaces.

Additionally, it may be because no up-front work has been done to identify the location of the contamination, excessive water, decontamination formulation, and manpower is often wasted on performing decontamination on surfaces where there may in fact be no CWA or other contamination present.

It may improve the efficiency and reduce the cost and logistical burden of performing decontamination by having a technology or system of technologies capable of detecting and informing the user of the precise location of the contamination on the surfaces.

SUMMARY OF THE INVENTION

The invention includes a method for efficiently decontaminating surfaces comprising using a device capable of determining a location where a contamination is present on a surface and decontaminating the location of the contamination.

Another embodiment of the method of this invention includes using a device capable of determining the location where contamination is present on a surface and, if contamination is not found, determining whether decontamination was successful.

Another embodiment of this invention includes a method for efficiently decontaminating surfaces comprising applying an indicator to a surface wherein said indicator provides an observable or machine readable response when a contamination is present on said surface, wherein said response is located relative to a location of said contamination, and decontaminating said location of said contamination. In a preferred embodiment this method includes applying said indicator that is commercially available from FLIR Detection, Inc. as Agentase Disclosure Spray. Another embodiment of this method includes reading the response by use of a machine. Another embodiment of this method includes providing a response that is colorimetric. In a more preferred embodiment of the method of this invention, the method provides analyzing whether said location of said response and said location of said contamination are the same location.

Another embodiment of the method of this invention includes applying an indicator (commercially available from FLIR Detection, Inc. as Agentase Disclosure Spray) to a surface wherein said indicator provides an observable or machine readable response when a contamination is present on said surface, wherein said response is located relative to a location of said contamination and, if no response is found, the decontamination procedure is determined to be effective. In a preferred embodiment of this invention, the method includes reading said response by a machine. Another embodiment of this method includes applying said indicator wherein the indicator is commercially available from FLIR Detection, Inc. as Agentase Disclosure Spray. Another embodiment of this method includes providing a response that is colorimetric. Another embodiment of this method includes analyzing whether said location of said response and said location of said contamination are the same location.

Another embodiment of this method includes applying an indicator to a surface wherein said indicator provides an observable or machine readable response when contamination is present, wherein said response is located relative to a location of said contamination and, if no response is found, the decontamination procedure is determined to be effective. Another embodiment of this invention provides reading said response is by a machine.

Another embodiment of this invention includes a method for efficiently decontaminating surfaces comprising applying an indicator to a surface wherein said indicator provides an observable or machine readable response when a contamination is present, wherein said response is relative to a location of said contamination, using a machine to read said response, sending the reading to a computer, providing a computer analysis of the reading wherein said computer determines a location of said response, transmitting said analysis to a decontaminating unit, and decontaminating said location of said contamination by using said decontaminating unit.

Another embodiment of the method of this invention includes applying an indicator to a surface wherein said indicator provides an observable or machine readable response when a contamination is present, wherein said response is located relative to a location of said contamination, using a machine to read the response, sending the reading to a computer, providing a computer analysis of the reading wherein said computer determines a location of said response, transmitting said analysis to a decontaminating unit, if a response is present, applying decontamination efforts by use of said decontamination unit, and if no response is present, the decontamination procedure is determined to be effective. In a preferred embodiment, this method includes using automated processes to perform the method for efficiently decontaminating surfaces, such as for example but not limited to, using a robotic arm to apply the indicator, and wherein said decontamination unit comprises one robotic spray arm and one or more robotic scrubbing arms preferably in communication with the robotic spray arm.

BRIEF DESCRIPTION OF THE DRAWINGS

FIGS. 1, 2, and three show the steps of the method of this invention. FIG. 1 shows a method of indicating contamination. 101 is a chemical indicator, 102 is a machine capable of reading an indicator, 103 is a military vehicle. 104 is a location of the military vehicle 103 that is contaminated as determined by an observable or machine readable response obtained from applying machine 102 in juxtaposition to the surface of the military vehicle 103.

FIGS. 4A., B., and C. show an automated efficient decontamination process of this invention wherein 112 is a chemical indicator, 111 is a machine capable of reading the indicator's response, 109 is a military vehicle, 110 is a location with an observable or machine readable response on the surface of the military vehicle 109, 113 is a decontamination unit for removing the contamination targeted at the location with the response, 115 is a chemical indicator that may be the same indicator as 112 or a different indicator, 116 is a computer to receive the location data of a response from machine 111, the computer 116 provides an analysis of the reading from machine 111 wherein the computer 116 determines a location of the response and transmits the analysis to a decontamination unit 113. FIG. 4A. shows a method of applying a chemical indicator 112, FIG. 4B. shows a method of decontaminating a military vehicle 109 by applying decontamination unit 113 to the location of the contamination. FIG. 4C. shows a method of ensuring that the decontamination step was successful by applying chemical indicator 115 to the surface of said military vehicle 109 subsequent to decontamination and applying the operation of machine 111 to obtain a machine readable response that is sent to said computer 116 for analyzing whether said decontamination step was successful (i.e. no contamination present upon the reapplication of said indicator 115 and use of machine 111).

In FIG. 5, 117 is a chemical indicator, 118 is the indicator's response that is observable or machine readable, 119 is a decontamination unit having a decontamination solution contained in an applicator. FIG. 5A. shows the process of applying the indicator 117 to the clothing worn by a human personnel. FIG. 5B. shows a human personnel with indicator 117 applied to his/her outer clothing. FIG. 5C. shows use of the decontamination unit 119 to remove the contamination targeted at the location indicated.

In FIGS. 6A. and B., 120 is a chemical indicator. FIG. 6A. is the process of applying the indicator 120 to a person (i.e. personnel). FIG. 6B. shows the result of applying the indicator 120 to the clothing of the person wherein the indicator did not respond because the contamination was successfully removed in the methods of this inventions shown in FIGS. 5A., B., and C.

In FIG. 7, an embodiment of how a decontamination process of this invention may be set-up, wherein step 121 is military vehicle undergoing a primary wash of its surface with water, step 122 is a military vehicle undergoing an application of indicator chemical to its surface after proceeding through step 121. Pathway A shows step 123 that is a military vehicle that was found to be substantially clean after proceeding through step 122, 124 is a military vehicle undergoing a final rinse with water after it has proceeded through step 123 of Pathway A or step 129 of Pathways B and C. Pathway B shows step 125 that is a military vehicle that was found to have a location with contamination present after proceeding through step 122, and step 126 is that military vehicle undergoing decontamination procedures that are targeted at a location with contamination present after proceeding through step 125. Step 127 is the military vehicle that is undergoing a rinse procedure performed after decontamination in step 126 or step 132. Step 128 shows a military vehicle undergoing an application of indicator to determine whether decontamination procedures were successful after proceeding through step 127. Step 129 shows a military vehicle that was found to be clean after step 128. Step 130 is a vehicle that was found to still have contamination after step 128. Step 131 shows a military vehicle that was found to have substantial locations where contamination was present after proceeding through step 122. Step 132 shows a military vehicle undergoing an extensive decontamination procedure. In a preferred embodiment, arrow 133 indicates the direction of the wind during the method of this invention. FIG. 7 shows that depending on the outcome of the methods of this invention, there are may be three possible routes of decontamination: (Pathway A.) is a route where no substantial contamination is revealed, (Pathway B.) some substantial contamination is present, and (Pathway C.) substantial contamination is present. After reapplication of indicator in step 128, the military vehicle will proceed to (Pathway D.) for further decontamination or (Pathway E.) if no contamination was observed.

FIGS. 8A, B, and C. show 3 different possible stages in the detection of a nerve agent simulant.

FIGS. 9A., B., and C. show 3 different stages in the decontamination of a nerve agent simulant that was found through a color response. FIG. 9(A. shows a contaminated white ceramic tile that has decontaminant applied to the contaminated locations identified by numerals 135, 136 and 137, which turns the chemical indicator solution a pink color (shown as a darker color in FIG. 9A.). FIG. 9(B. shows a decontaminated white ceramic tile that turned clear at locations 135, 136 and 137 after the decontaminating procedure. FIG. 9C. shows a white ceramic tile after rinsing the indicator and decontaminant from the surface of the tile with clean water, wherein 135 is location 1 from FIG. 8, 136 is location 2 from FIG. 8, and 137 is location 3 from FIG. 8.

FIGS. 10A, B, and C show 3 different stages in the determination of whether decontamination was successful.

DETAILED DESCRIPTION OF THE INVENTION

The current invention includes a process that minimizes decontamination efforts and logistics. The invention includes first finding where contamination is located. After discovery of contamination, the user may focus decontamination efforts on the area that was identified as contaminated. Then, an optional step after decontamination may ensure that the surface is free of contamination.

The current invention includes a process for minimizing decontamination efforts and showing that decontamination has occurred. Based on thorough decontamination protocols set forth by currently adopted doctrine in the CBRN Decontamination Multiservice Tactics, Techniques, and Procedures for Chemical, Biological, Radiological, and Nuclear Decontamination Field Manual (FM 3-11.5 April 2006), the average vehicle requires 500 gallons of water, 30 personnel in protective equipment, and 4-6 hours of effort during Detailed Equipment Decontamination. Decontaminating 10 vehicles uses approximately 4700-5100 gallons of water, requires 27-31 people, and 35 to 50 man hours, 1,000 to 3,000 pounds of decontamination material and may cost approximately $40,000. The CBRN Decontamination Multiservice Tactics, Techniques, and Procedures for Chemical, Biological, Radiological, and Nuclear Decontamination Field Manual (FM 3-11.5 Apr. 2006) is incorporated by reference.

Using the current invention, required resources may be reduced to 700-950 gallons of water (85.1%-81.4% reduction), 12-13 people (about 55.6%-58.1 i;'(; reduction), 15-21 (about 53.1%-58% reduction) man hours, 250-1000 (about 66'/i)-75% reduction) pounds of decontamination material, a cost of approximately $15,000 (about 62.5% reduction). The invention may reduce the time, cost, man-power, and resource consumption of traditional decontamination. It may focus decontamination resources in contaminated areas which may minimize wasted efforts. The current invention may provide for quick post-decontamination validation that contamination may be substantially removed and may shorten the need for vapor off-gas monitoring. The decontaminants used may be highly corrosive. By lowering the amount used, there may be less corrosive damage to equipment. The current invention may lessen the environmental impact of decontaminant runoff. Further, uncontaminated materials or assets may be declared dean and may be returned to their use without requirement for decontamination, which may save time, effort and money. As used herein, the term "indicator" includes but is not limited to anything that responds to an analyte of interest with an observable or machine readable response. This response can be but is not limited to chemical processes that results in changes in absorption wavelength, changes in ultraviolet, visible, or infrared fluorescence intensity or wavelength, phosphorescence, changes in temperature, thickening, thinning or any chemical reaction capable of being observed or machine readable. An indicator may be active or passive. An indicator may be applied before or after the contamination has occurred. An indicator includes but is not limited to the Agentase Disclosure Spray ("ADS") commercially available from FLIR Detection, Inc., Pittsburgh, Pa., USA. ADS may be a sprayable, water-based formulation that uses enzymes to detect the location of chemical agents on surfaces by changing color (absorbance wavelength). ADS Nerve indicator may be used to detect nerve agents. An enzyme, which includes but is not limited to acetylcholinesterase and urease, is inhibited by organophosphorus nerve agent compounds. This inhibition may drive a subsequent pH change, and a colorimetric pH-responsive dye present in the indicator changes color. This indicator, when applied to a surface, may go down yellow and may turn red in the presence of a nerve agent. ADS may be considered a contact based sensor. U.S. Patent Publication. No. US 2010/0227345 describes the ADS and the process of how the ADS indicator works. The text of U.S. Patent Publication No. US 2010/0227345 is incorporated by reference into this specification as if fully written herein. In a preferred embodiment, the ADS is an aqueous enzyme based sensor comprising one or more enzymes, and at least one indicator compound capable of indicating a reaction of at least one of said enzymes with at least one target analyte, wherein the enzyme and the indicator are capable of being delivered to a surface having the target analyte. The ADS based sensor is capable of being sprayed onto said surface in order to detect the presence of a target chemical. Further, the ADS based sensor is capable of detecting an enzyme specific substrate as said analyte. Further, the ADS based sensor comprising of one or more enzyme specific substrates in which the enzyme based sensor detects enzyme inhibition. The ADS based sensor includes wherein said enzyme is at least one selected from the group consisting of cholinesterases, ureases, peroxidases, proteases, and combinations thereof. In a more preferred embodiment, said enzyme is at least one selected from the group consisting of ureases, peroxidases, and proteases, and further wherein the enzyme is at least one selected from the group consisting of cholinesterases, peroxidases, and proteases. The enzyme specific substrate is selected from the group consisting of acetylcholine, butyrylcholine, urea, N-benzoyl arginyl ethyl ester, hydrogen peroxide, and N-benzoyl arginyl p-nitroanilide for producing acid or base or chromogenic or oxidized product upon enzymatic reaction. In a another embodiment of the ADS based sensor said indicator is a pH indicator dye that is selected from the group consisting of cresol red, phenol red, metacresol purple, neutral red, and curcumin, or a pH sensitive fluorescent dye selected from the group consisting of carboxy-seminaphthorhodafluor and fluorescein, or wherein the indicator is a redox dye selected from the group consisting of guaiacol, 4-aminoantipyrine, and 3-(N-Ethyl-3-methylanilino)-2-hydroxypropanesulfonic acid and N-Ethyl-N-(2-hydroxy-3-sulfopropyl)-3,5-dimethoxyaniline sodium salt. Preferably, the ADS based sensor includes wherein the indicator senses at least one of a visible color change, a change in pH, oxidation state or substrate concentration.

Contact based sensor may be more sensitive than standoff detectors. Contact based sensors may be able to detect less volatile contaminants by being in physical contact with the contamination and may not have to rely on the contaminant off-gassing from the surface. Further, contact based sensors may be able to overcome masking effects present on the surface with the contamination. The contact based sensors may interact with the contamination on the surface in discrete locations while non-contact based sensors may read broader areas and space in between the detector and the surface. This added area and space may cause false reading due to presence of other background chemicals.

Many other types or classes of indicators are known to those skilled in the art. Indicators includes those that change directly based on pH, for example but no limited to: bromocresol purple which changes to purple above pH 6.8 and to yellow below pH 5.2, methyl red which changes to red under pH 4.4 and yellow over pH 6.2, brilliant yellow which changes to yellow under 6.5 and reddish orange above pH 8.0, and phenol red which changes to yellow under pH 6.8 and red above pH 8.2. Indicators include other chemicals that may directly bind to the target toxic chemical itself and produce an observable or machine readable response or those that produce a temperature response. Indicators include coupled reactions. Indicators may use an enzyme to drive a pH change in the indicator and then a pH dye used to indicate the change to the user. The specific pH the indicators operate at may not be absolutely necessary; the indicator may only require that there is a change in the pH. Indicators may use an enzyme to oxidize or inhibit oxidation of a substrate, whereby the oxidation or inhibition of oxidation of the substrate creates a response in the indicator. The oxidation of the substrate may mean either there is contamination or there is no contamination.

As used herein, a "machine" capable of observing an indicator's machine readable response includes but is not limited to stand-off Raman detectors, cameras, spectrometers, thermal cameras, the Joint Chemical Agent Detector (JCAD), the improved Chemical Agent Monitor (ICAM), the Avalon standoff Raman spectrometer, Hyperspectral Imagers, identiFINDER and night vision devices.

Machines that may read a colorimetric response from an indicator, for example but not limited to ADS, includes cameras and spectrophotometers. A thermal camera can read a temperature response of an indicator.

As used herein, the term "contamination" includes but is not limited to the presence of an unwanted constituent. The constituent includes but is not limited to Chemical Warfare Agents, Biological Warfare Agents, toxic industrial chemicals, radioactive substances, infectious diseases, or other foreign compounds.

As used herein, the term "decontamination" includes the process of cleansing an object or substance to remove contaminants. These contaminants includes but are not limited to micro-organisms, hazardous materials, Chemical Warfare Agents, Biological Warfare Agents, toxic industrial chemicals, radioactive substances, agents of infectious diseases, infectious diseases, and other foreign compounds. Decontamination includes some of the processes in the CBRN Decontamination Multiservice Tactics, Techniques, and Procedures for Chemical, Biological, Radiological, and Nuclear Decontamination Field Manual (FM 3-11.5 Apr. 2006). Decontamination includes Spot Decontamination provided in CBRN Decontamination Multiservice Tactics, Techniques, and Procedures for Chemical, Biological, Radiological, and Nuclear Decontamination Field Manual (FM 3-11.5 April 2006). Aircrews and aircraft ground support crews can use spot decontamination as an immediate measure to remove contamination from critical locations. Spot decontamination is performed to limit the spread of contamination on aircraft that requires servicing between sorties, to support ingress and egress of aircraft by crews and passengers, and when performing pre- and post-flight inspections. Spot decontamination reduces the contamination on the areas that must be touched during servicing. Procedure (1) Ensure that sufficient quantities of soapy water or applicable aircraft cleaner and fresh water are available. (2) Scrub service areas with soapy water using brushes, rags, or sponges until deposited material, dirt, and grime are removed. (3) Rinse areas with fresh water from a bucket or hose. (4) Ensure that service providers decontaminate gloves (SDK, soapy water, or high-test hypochlorite [HTH] solution). (5) Perform service on the aircraft. (6) Decontaminate runoff by applying a standard or nonstandard decontaminant to the deck/ground/airfield. Runoff can be hosed overboard or into collection sumps. If runoff is hosed without prior decontamination, it should be treated as contaminated.

As used herein, the term "surfaces" includes but is not limited to the outside part or uppermost layer of some object. Objects with a surface includes but are not limited to, floors, walls, ceilings, vehicles, gloves, protective suits, articles of clothing, skin, windows, doors, shelves, tables, counters, computers, tanks, helicopters, planes, motorcycles, bicycles, glassware, glasses, helmets, paper, weapons, vegetation, soil, carpet, and many others.

As used herein the term "decontaminating unit" includes but is not limited to robots, robotic spray arms, robotic scrubbers and persons directed by audible or visual cues that perform decontamination procedures.

Figure 1:
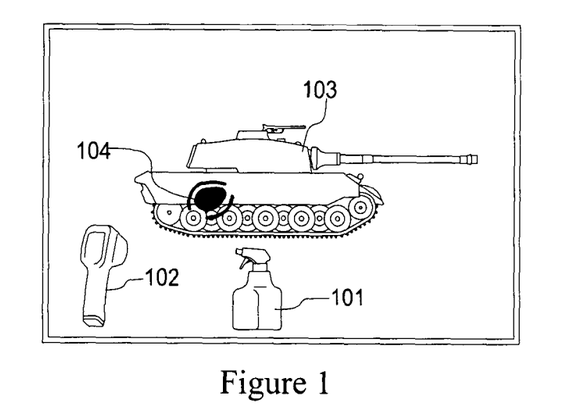

The current invention minimizes water and decontaminant use by indicating a contaminated location to a user to focus efforts at that location. Thus, use of this method of this invention lessens the use of decontaminant on the clean areas of the surface which do not show substantial contamination. In the current invention, an operator, user, computer, or robot may first apply an indicator to the surface to analyze whether the surface has contamination by observing the response of the indicator. If the response of the indicator does specify there is substantial contamination present, the identity of where the contamination is located relative to the location of the indicator's response is set forth in FIG. 1.

This indicator compound may react with the chemical that is of interest to the user. The reaction may produce a response (location identified as 104 in FIG. 1). The response may be colorimetric, heating, cooling, thickening, thinning, phosphorescent fluorescent or absorptive. The changes may be observable by a person or machine readable. However, if they cannot be observed by a person, a machine may be used that may read the response (102, FIG. 1). A colorimetric response may be read by a camera. Then the operator, user or robot may remember the location of the contamination, or it may be automatically marked by software in the device which may relay the location of the contamination to another operator or robotic system that may perform the decontamination operation. If no substantial contamination is detected, then the user, operator or robot may not have to decontaminate that surface.

Figure 2:
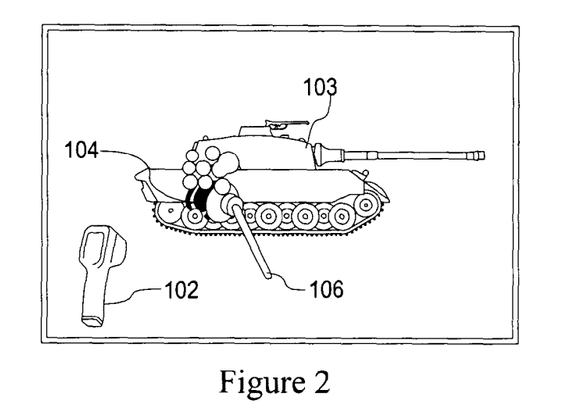
FIG. 2 shows a method of decontaminating said military vehicle 103 at location with an observable or machine readable response 104 on the military vehicle 103 using a decontamination unit 106 to remove the contamination targeted at the location with the response.
Figure 3:
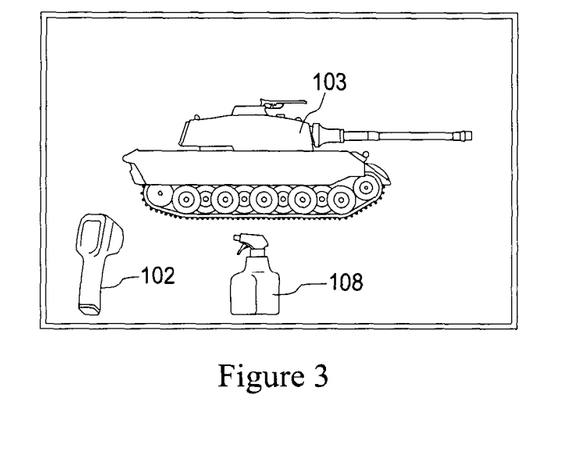
FIG. 3 shows a method of ensuring decontamination efforts were successful by applying chemical indicator 108 (which may be the same indicator or a different indicator than indicator 103) to said military vehicle 103 subsequent to said decontamination of said military vehicle, and using a machine 102 that is capable of reading the indicator's response after it is applied to the military vehicle 103.

If contamination is detected by the indicator, decontamination procedures may be instituted. When decontamination procedures are instituted they may be targeted at the contaminated location (FIG. 2). During decontamination, the indicator may be washed off and/or deactivated. The operator, user, computer or robot may remember where the location is during decontamination efforts. Then, after the final rinse with water, indicator can be applied to the previously contaminated area to determine if the decontamination efforts successfully removed a substantial amount of the contamination (FIG. 3).

Figure 4:
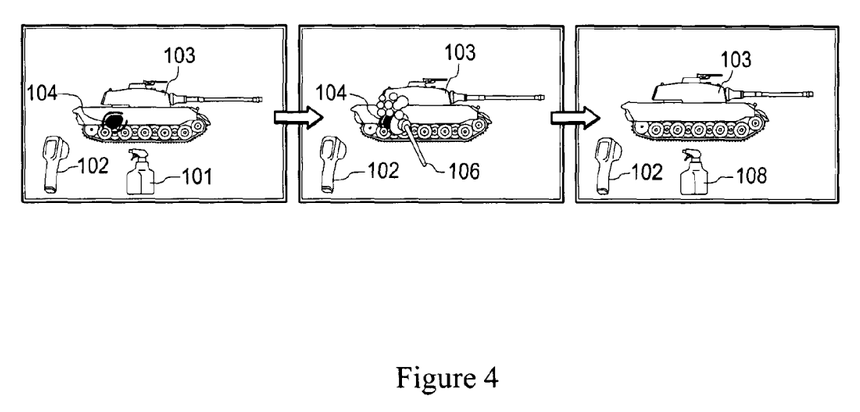

The current invention may be completely automated (see FIG. 4). A computer (116) may direct a robot to apply the indicator (112), and then it may determine if there is contamination (110) through a machine (111) that is capable of reading the indicator response. In the case of a colorimetric response, for example but not limited to ADS, it may be read by a camera. Then it may store the location data in a computer (116). The computer (116) may then use this location data to direct decontamination operations (113, FIG. 8B.) to the contaminated area (110). If required, the computer (116) may apply the indicator (112) to the surface by using the stored location data and determine if the contamination was successfully removed (FIG. 8C.).

Figure 5:
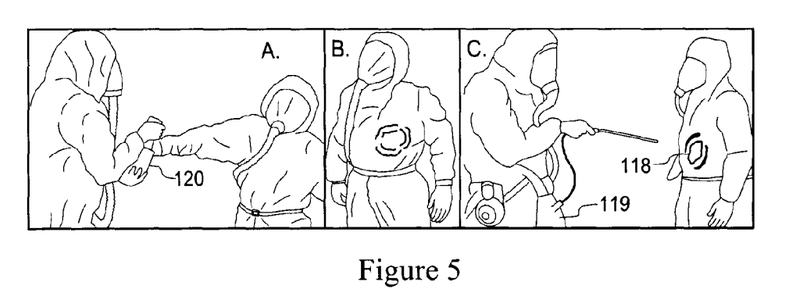
FIG. 5 shows a method of efficient personnel decontamination of this invention.

The current invention may be used similarly on personnel. In the current invention, an operator, user, or robot may first apply an indicator compound to the surface to analyze whether the surface has contamination and, if it does, where the contamination may be located (see FIG. 5). This indicator compound may react with the chemical of interest to produce a response (118). A machine may be used to read the response. If no substantial contamination is observed or machine readable, then the user, operator, computer, or robot may not have to decontaminate that surface.

Figure 6:
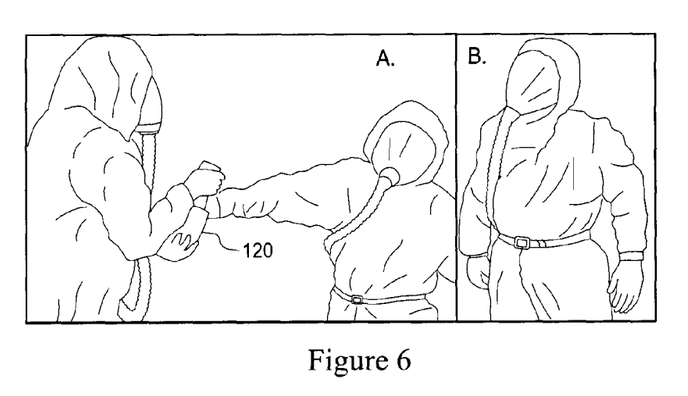
FIG. 6 shows a method of ensuring that the decontamination method shown in FIGS. 5A., B., and C. were successful.

If contamination is detected by the indicator, decontamination procedures may be instituted. When decontamination procedures are instituted they may be targeted at the contaminated location (see 118, FIG. 5). During decontamination, the indicator may be washed off and/or deactivated. The operator, user or robot may remember where the area is during decontamination efforts. Then, after the final rinse with water, indicator may be applied to the previously contaminated area to determine if the decontamination efforts successfully removed a substantial amount of the contamination (see FIG. 6).

Figure 7:
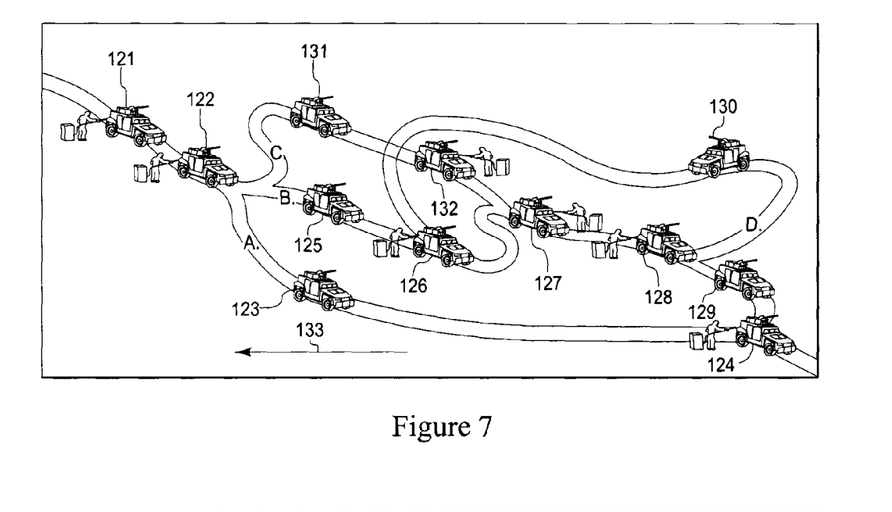
FIG. 7 is a pictorial representation of the method of decontaminating a vehicle (object) of this invention under three different situations set forth as pathways "A.", "B.", or "C.".

Depending on the presence of contamination there may be different routes for a military vehicle (121) to follow during a decontamination procedure of this invention. FIG. 7 shows an embodiment of the methods of this invention wherein a decontamination process is carried out. A military vehicle will first undergo a primary wash of the vehicle's surface (121). Then an application of indicator will be applied to the surface of the military (122) vehicle after proceeding through 121. Depending on the outcome of 122 there are may be three possible routes of decontamination: (A.) is a route where no substantial contamination is revealed, (B.) is a route where some substantial contamination is present, and (C.) is a route where substantial contamination is present which where traditional decontamination procedures may assume the worst case scenario with an extensive decontamination targeting substantial portions of a vehicle. This invention may enable a triage prior to decontamination which may allow substantial savings in resources since an extensive decontamination may not be required in the case of a clean vehicle. If no contamination was observed the military vehicle will proceed down path A to 123. The military vehicle will undergo a final rinse (124) after it has proceeded through 123 and be ready to go back into service. This may save time since the vehicle did not have to undergo decontamination procedures. If a military vehicle was found to have a location with contamination present after proceeding through 122 it will proceed down path B to 125. Then the military vehicle may undergo a decontamination procedure that is targeted at a location with contamination present (126) after proceeding through 125. The military vehicle will undergo a rinse procedure (127) performed after decontamination in 126. In addition to traditional decontamination procedures this invention may add a feedback loop to the standard decontamination procedure. The military vehicle will undergo another application of indicator to determine whether decontamination procedures were successful (128) after proceeding through 127. After reapplication of indicator in 128 the military vehicle will proceed to (D.) for further decontamination or (E.) if the vehicle is determine to not have any substantial contamination. If no substantial contamination is present the military vehicle will be found to be clean after 128 and proceed down path E. to 129. Then after 129 it will proceed to 124 for a final rinse and be put back into service. Path B. may save time by allowing less than full decontamination procedures. If after 128 the military vehicle was found to still have contamination it will proceed down path D. to 130. This vehicle will then re-enter the process at 126. This operation will ensure that decontamination procedures were effective to ensure the health and safety of operators of those vehicles. If after 122, substantial contamination is present the military vehicle will proceed down path C to 131. The military vehicle will undergo an extensive decontamination procedure (132) after 131. Then the vehicle will enter the process at 127. 133 indicates the preferred direction of the wind when setting up a decontamination process.

Another embodiment includes a method for efficiently decontaminating surfaces comprising a computer controlled robotic sprayer arm, such as but not limited to the Easypaint Robot (commercially available from SAMES Technologies, Meylan, France), applying an indicator, such as but not limited to Agentase Disclosure Spray (commercially available from FLIR Detection, Inc., Pittsburgh, Pa., USA), to a surface. Wherein, the indicator provides an observable or machine readable response, such as but not limited to a color change, when a contamination is present. Wherein said response may be relative to a location of said contamination. The location of the indicator may be the same location, below, above, to the left, to the right, of the contamination. The location of the response may change due to the chemistry involved, the amount of indicator applied and the grade of the surface. Then a computer may control a machine, such as but not limited to a charge-coupled device (CCD) sensor, to read said response. One skilled in the art will understand that a CCD can be used to read a color response. The machine reading, such as but not limited to an image, may then be sent to a computer. Computer programs such as but not limited to MatLab or Labview may be used to determine the location of color within an image. The computer may analyze the response by determining the regions of the response wherein the response is present. Such as but not limited to determining where the response color is located within the image taken by the CCD. The computer may then determine where the location of the contamination is based on the indicator's response. The computer may control a robotic spray arm filled with decontaminating solution to spray the location that is contaminated based on the indicator's response. After the computer sprays the location with the robotic arm it may then scrub the spot with a robotic brush arm. After scrubbing it may spray the location that is contaminated with a robotic spray arm containing water to rinse the solution off.

A method is provided for efficiently decontaminating surfaces comprising applying an indicator to a surface wherein the indicator provides an observable or machine readable response when a contamination is present on the surface, wherein the response is located relative to a location of the contamination; and decontaminating the location of the contamination. Preferably, the method includes wherein the indicator is an aqueous based sensor. Preferably, the method includes wherein the response is read by a machine, or wherein the response is colorimetric. The method as described herein includes wherein the location of the response and the location of the contamination are the same location. The method includes applying an indicator to a surface wherein the indicator provides an observable or machine readable response when a contamination is present on the surface, wherein the response is relative to a location of the contamination; and if no response is found, the decontamination procedure is determined to be effective. This method preferably includes wherein the indicator is an aqueous based sensor. This method preferably includes wherein the response is read by a machine or is wherein the response is colorimetric. The location of the response and the location of the contamination are the same location.

Another embodiment of this invention provides a method for efficiently decontaminating surfaces comprising applying an indicator to a surface wherein the indicator provides an observable or machine readable response when a contamination is present on the surface, wherein the response is relative to a location of the contamination; using a machine to read the response; sending the reading to a computer; providing a computer analysis of the reading wherein the computer determines a location of the response; transmitting the analysis to a decontaminating process unit; and decontaminating the location of the contamination by using the decontaminating process unit. Preferably this method further comprises applying an indicator to a surface wherein the indicator provides an observable or machine readable response when a contamination is present on the surface, wherein the response is relative to a location of the contamination; using a machine to read the response; sending the reading to a computer; providing a computer analysis of the reading where the computer determines a location of the response; transmitting the analysis to a decontaminating process unit; and if a response is present, applying further decontamination; and if no response is present, the decontamination procedure is determined to be effective. In a more preferred embodiment of this method, as described herein, the method further comprises using automated processes to perform the steps of the method. Such automation includes but is not limited to, for example, using at least one robotic arm to apply the indicator, or wherein the decontamination processing unit comprises at least one robotic spray arm; and one or more robotic scrubbing arms in communication with the robotic spray arm.

EXAMPLES

Example 1

Figure 8:
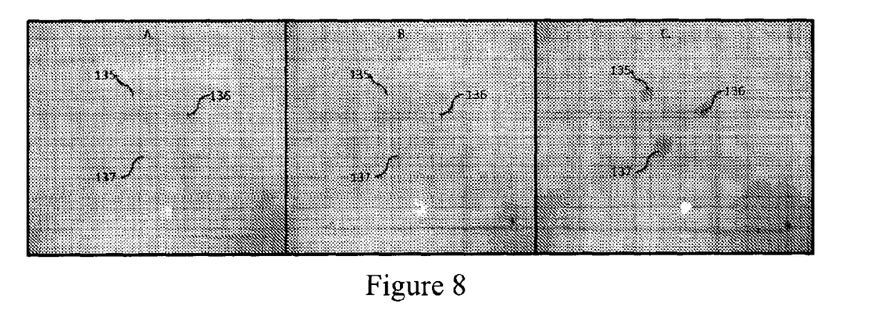
FIG. 8A. is a picture of a white ceramic tile contaminated with a colorless chemical agent simulant at locations identified by numerals 135, 136 and 137.
FIG. 8B. is a picture of a contaminated white ceramic tile after it had indicator chemical applied to the surface of the tile.
FIG. 8C. is a picture of a white ceramic tile after it had developed a color response at the locations of where the nerve agent simulant was applied at locations 135, 136 and 137. Numeral 135 represents the location 1 where contamination of nerve agent simulant was applied in FIG. 8A. Numeral 136 shows the location 2 where contamination of nerve agent simulant was applied in FIG. 8A. Numeral 137 shows location 3 where contamination of nerve agent simulant was applied in FIG. 8A.

A surface (white ceramic tile) is contaminated with a chemical agent simulant, in this case an organophosphorus nerve agent pesticide simulant, paraoxon (see FIG. 8). An Indicator formulation (Nerve Agent—Agentase Disclosure Spray) is applied to the surface via spraying (FIG. 8). Within 1-5 minutes, a colorimetric response develops (FIG. 8). In this case, the response is a visible color change from yellow to red in the locations of contamination (positive response).

Figure 9:
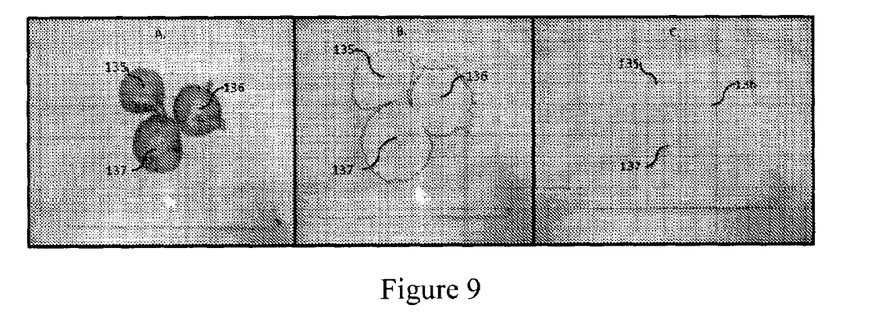

Based on the indicator response, a chlorine-based decontamination solution (commercial bleach) was applied to the localized contamination locations indicated by the liquid indicator formulation. Within 10 seconds, the process first changes the indicator pink (dark color set forth in FIG. 9A.) then clear, at about 2 minutes (FIG. 9B.) where decontaminant is applied, as the dyes in the indicator formulation are chemically oxidized and lose their color. Both the indicator and decontaminant are then removed by a clean water rinse in the final stage of the process (FIG. 9C.).

Figure 10:
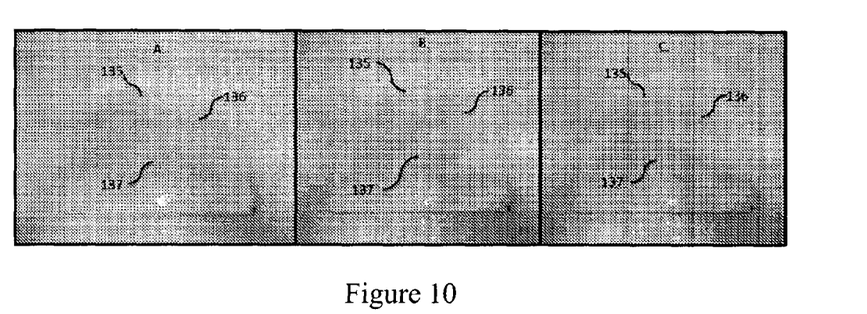
FIG. 10A. shows a ceramic white tile that has gone through a decontamination procedure and was rinsed and now has indicator chemical applied.
FIG. 10B. shows a ceramic white tile that had not developed a color response on its surface.
FIG. 10C. shows a ceramic tile after a clean water rinse to remove the indicator chemical, wherein 135 is location 1 from FIG. 8, 136 is location 2 from FIG. 8, and 137 is location 3 from FIG. 8.

Following the rinse, indicator was applied to the surface (see FIG. 10A.). The targeted application of the bleach solution successfully decontaminated the simulant, and no positive response (a red color) is observed (see FIG. 10B.). The surface is clean. A final rinse is performed with clean water to remove the indicator (see FIG. 10C).

Example 2

A surface (white ceramic tile) is contaminated with a chemical agent simulant, in this case a Mustard Agent simulant, 2-CEPS (2-chloroethylphenyl sulfide). An Indicator formulation (Blister Agent—Agentase Disclosure Spray) is applied to the surface via spraying. Within 1-5 minutes, a colorimetric response develops. The Blister Agent Disclosure Spray goes down red and transitions to yellow if the surface does not contain substantial contamination. If there is substantial contamination the indicator will remain red and not transition to yellow.

Based on the indicator response, a chlorine-based decontamination solution (commercial bleach) was applied to the localized contamination locations indicated by the liquid indicator formulation. Within 10 seconds, the process first changes the indicator purple then clear, after about 2 minutes, where decontaminant is applied, as the dyes in the indicator formulation are chemically oxidized and lose their color. Both the indicator and decontaminant are then removed by a clean water rinse in the final stage of the process.

Following the rinse, indicator was again applied to the surface. The targeted application of the bleach solution successfully decontaminated the simulant, no positive response (red color after 5 minutes of monitoring) from the indicator is observed. The surface is clean. A final rinse is performed with clean water to remove the indicator.

Example 3

A surface (white ceramic tile) is contaminated with a chemical agent simulant, in this case an organophosphorus nerve agent pesticide simulant. An Indicator formulation (Agentase Disclosure Spray) is applied to the surface via spraying from a robotic applicator. Over several minutes, a colorimetric response develops. In this case, the response is a visible color change from yellow to red in the locations of contamination. The colorimetric response is monitored by a camera connected to a computer. The computer will specify the locations where the response is substantially present and determine their location.

Based on the location the computer has determined, the computer directs a system to apply a chlorine-based decontamination solution (commercial bleach) to the contaminated locations indicated by the liquid indicator formulation. This process first changes the indicator pink then clear where decontaminant is applied, as the dyes in the indicator formulation are chemically oxidized and lose their color. The computer then removes both the indicator and decontaminant by a clean water rinse in the final stage of the process.

Following the rinse, the computer applies indicator via a robotic applicator to the surface. The targeted application of the bleach solution successfully decontaminated the simulant, no positive response is observed. The surface is clean. The computer then performs a final rinse with clean water to remove the indicator.

Example 4

A surface (white ceramic tile) is contaminated with a chemical agent simulant, in this case an organophosphorus nerve agent pesticide simulant, DFP (Diisopropylfluorophosphate). A hyperspectral imager capable of determining whether contamination is present is used to read the tile. The device takes a hyperspectral image of the tile. Using spectral information it determines where the simulant is located.

Based on the location, a chlorine-based decontamination solution (commercial bleach) is applied to the contamination locations indicated by the hyperspectral imager. The decontaminant is removed by a clean water rinse in the final stage of the process.

Following the rinse, a hyperspectral imager capable of determining whether contamination is present is used to read the tile. The targeted application decontaminant solution successfully decontaminated the simulant, and the hyperspectral imager does not read any simulant on the tile. The surface is clean.

Example 5

A surface (white ceramic tile) is contaminated with radioactive materials. An identiFINDER instrument, commercially available from FUR, which, is capable of detecting whether radioactive contamination is present, is used to read the tile to look for contamination. The identiFINDER instruments quickly detect, locate and identify radiation sources. The identiFINDER instrument contains preferably on-board Bluetooth, web server and GPS technologies and produce rapid visible, audible and tactile alerts that expedite response measures. For example but not limited to, the identiFINDER R 300 is a belt wearable Spectroscopic Personal Radiation Device (SPRD). It provides continuous detection capability and the fast identification of radioactive material which supplies critical information to the user in the field, enabling them to make a next step determination. The unit contains one 13 mm (0.5")×17 mm (0.7")×5 mm (0.2") CZT crystal with excellent resolution for identification of the radioactive material while two other detectors of the same size are used for detection and dose rate calculation. For example, the instrument can be equipped with an optional 3He neutron detector. Due to its small size and rugged design, a identiFINDER R 300 can be deployed in place of existing PRD technologies with the added capability of identifying the isotope present. These features make it an ideal choice for those on the front lines of homeland security such as emergency responders and border patrol agents Based on the location, a decontamination solution is applied to the contamination locations indicated by the identiFINDER, the decontaminant is removed by a clean water rinse in the final stage of the process.

Following the rinse, the identiFINDER is used to determine whether radioactive contamination is present. The targeted application decontaminant solution successfully decontaminated the simulant, and no radioactive material is detected on the tile. The surface is clean.

Example 6

An indicator coating is applied to a tailgate of a military High Mobility Multipurpose Wheeled Vehicle (HMMWV) also known as a "Humvee". The coating comprises a removable polyurethane coating that contains Organophosphorus Acid Anhydrolase (OPAA), Dehalogenase (DHG) and methyl red. The coating is allowed to dry on the surface. One day later a portion of the tailgate was contaminated with a nerve agent simulant, DFP. Within 1-10 minutes, a colorimetric response develops. In this case, the response is a visible color change from yellow/brown to red in the locations of contamination.

Based on the indicator response, the coating is removed from the contaminated area. Then a chlorine-based decontamination solution (commercial bleach) was applied to the exposed tailgate section. A clean water rinse is performed to remove the decontaminant. The surface was dried and the indicator coating was reapplied only to the area that was removed.

Two weeks later, an HD simulant, 2-CEPS, was applied to a different area of the tailgate that was not contaminated the first time. Within 1-10 minutes, a colorimetric response develops. In this case, the response is a visible color change from yellow/brown to red in the locations of contamination.

Based on the indicator response, the coating is removed from the contaminated area. Then a chlorine-based decontamination solution (commercial bleach) was applied to the exposed tailgate section. ADS Blister Agent indicator is then applied to the coating to ensure decontamination procedures were successful. No color response from the ADS is observed. Then a clean water rinse is performed to remove the indicator. The surface is dried, and the indicator coating was reapplied only to the area that was removed.

Two months later, a section of the tailgate was contaminated in one area with DFP and, in a different area, 2-CEPS. Within 1-10 minutes, a colorimetric response develops at both locations. In this case, the response is a visible color change from yellow/brown to red in the locations of contamination.

Based on the indicator response, the coating is removed from the contaminated areas. Then a chlorine-based decontamination solution (commercial bleach) was applied to the exposed tailgate section. Blister Agent ADS indicator is then applied to the coating to ensure decontamination procedures were successful. No color response from the ADS is observed. Then a clean water rinse is performed to remove the indicator. Then, Nerve Agent ADS indicator is applied to the coating to ensure decontamination procedures were successful. No color response from the ADS is observed. Then a clean water rinse is performed to remove the indicator. The surface is dried, and the indicator coating was reapplied only to the area that was removed.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value.

The use of the terms "a" and "an" and "the" and similar referents in the context of describing the invention are to be construed to cover both the singular and the plural, unless otherwise indicated herein or clearly contradicted by context.

Whereas particular embodiments of the instant invention have been described for the purposes of illustration, it will be evident to those persons skilled in the art that numerous variations and details of the instant invention may be made without departing from the instant invention as defined in the appended claims.

What is claimed is:

1. A method for efficiently decontaminating discrete surfaces of military equipment while in the field, the method comprising:
    applying a chemical warfare agent (CWA) indicator to a surface of military equipment;
    chemically reacting the CWA indicator with a CWA associated with a discrete portion of the surface of the military equipment to provide an observable or machine readable response in commensurate scope with the discrete portion of the contamination; and
    precisely decontaminating the discrete portion of the surface of the military equipment using decontaminant without exposing other surface portions exhibiting no response to the decontaminant.

2. The method of claim 1 wherein said indicator is an aqueous based sensor.

3. The method of claim 1 wherein said response is read by a machine.

4. The method of claim 1 wherein said response is colorimetric.

5. The method of claim 1 further comprising ceasing the decontamination when no readable response is observed.

6. The method of claim 1 further comprising:
    using a machine to read the response;
    sending the reading to a computer;
    providing a computer analysis of the reading where said computer determines a location of the discrete portion of the surface of the military equipment associated with the contaminant;
    transmitting said analysis to a decontaminating process unit; and
    if a response is present, applying further decontamination; and
    if no response is present, the decontamination method is determined to be effective.

7. The method of claim 6 further comprising using at least one robotic arm to apply the indicator.

8. The method of claim 6 wherein said decontamination processing unit comprises:
    at least one robotic spray arm; and
    one or more robotic scrubbing arms in communication with said robotic spray arm.

9. The method of claim 1 further comprising using automated processes to perform the method.

* * * * *

UNITED STATES PATENT AND TRADEMARK OFFICE
CERTIFICATE OF CORRECTION

PATENT NO. : 9,827,601 B2  Page 1 of 1
APPLICATION NO. : 14/733084
DATED : November 28, 2017
INVENTOR(S) : Robert J. Sovesky et al.

It is certified that error appears in the above-identified patent and that said Letters Patent is hereby corrected as shown below:

Column 1, Line 22 - Replace "Warf are Agents" with --Warfare Agents--

Column 6, Line 6 - Replace "55.6%-58.1 i;'" with --55.6%-58.1 I;'--

Column 6, Line 21 - Replace "declared dean" with --declared clean--

Signed and Sealed this
Third Day of July, 2018

Andrei Iancu
*Director of the United States Patent and Trademark Office*